United States Patent
Tokunaga et al.

(10) Patent No.: US 7,038,056 B2
(45) Date of Patent: May 2, 2006

(54) METHOD FOR PREPARING A 7-QUINOLINYL-3,5-DIHYDROXYHEPT-6-ENOATE

(75) Inventors: Kenichi Tokunaga, Chiba (JP); Masami Kozawa, Chiba (JP); Kenji Suzuki, Chiba (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 208 days.

(21) Appl. No.: 10/473,132

(22) PCT Filed: Mar. 22, 2002

(86) PCT No.: PCT/JP02/02779

§ 371 (c)(1),
(2), (4) Date: Oct. 6, 2003

(87) PCT Pub. No.: WO02/081451

PCT Pub. Date: Oct. 17, 2002

(65) Prior Publication Data

US 2005/0014947 A1 Jan. 20, 2005

(30) Foreign Application Priority Data

Apr. 5, 2001 (JP) .............................. 2001-106820

(51) Int. Cl.
*C07D 215/14* (2006.01)
(52) U.S. Cl. ..................................................... 546/174
(58) Field of Classification Search ................. 546/174
See application file for complete search history.

(56) References Cited

U.S. PATENT DOCUMENTS 4,645,854 A * 2/1987 Verhoeven et al. ........... 560/60

(Continued)

FOREIGN PATENT DOCUMENTS

EP 164049 12/1985

(Continued)

OTHER PUBLICATIONS

English Translation of JP 08-92217, Apr. 9, 1996.*

(Continued)

*Primary Examiner*—Fiona T. Powers
(74) *Attorney, Agent, or Firm*—Oblon, Spivak, McClelland, Maier & Neustadt, P.C.

(57) ABSTRACT

A method for preparing a 7-quinolynyl-3,5-dihydroxyhept-6-enoate useful as an intermediate for pharmaceuticals, in high yield and in high purity, is presented. It is a method for preparing a 7-quinolinyl-3,5-dihydroxyhept-6-enoate represented by the formula (IV):

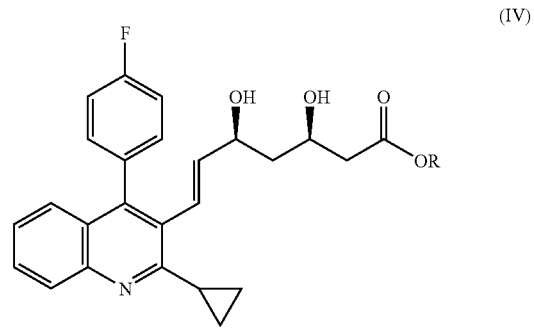

(IV)

(wherein R represents an alkyl group or an aryl group), characterized in that a compound represented by the formula (I):

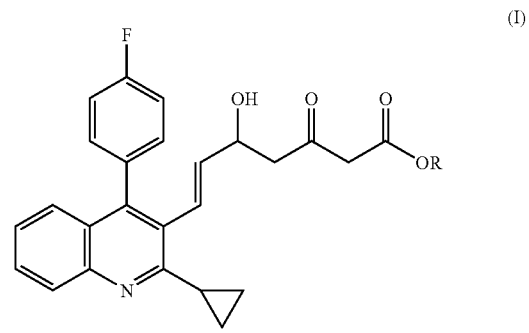

(I)

(wherein R is as defined above), or a compound represented by the formula (II):

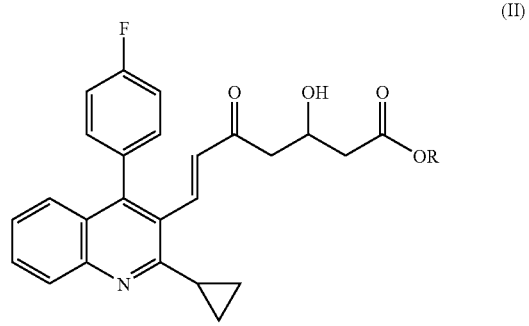

(II)

(wherein R is as defined above), is reduced by sodium borohydride in the presence of a boron compound represented by the formula (III):

$$R'OBR''_2 \quad (III)$$

(wherein R' and R" represent independently an alkyl group), and then the resultant reaction mixture is treated with an aqueous solution of hydrogen peroxide.

6 Claims, No Drawings

U.S. PATENT DOCUMENTS

| | | | |
|---|---|---|---|
| 5,011,930 A * | 4/1991 | Fujikawa et al. | 546/101 |
| 5,284,953 A * | 2/1994 | Ohara et al. | 546/173 |
| 5,753,675 A * | 5/1998 | Wattanasin | 514/311 |
| 6,946,557 B1 * | 9/2005 | Onishi et al. | 546/173 |
| 2004/0030139 A1 * | 2/2004 | Hara et al. | 546/174 |

FOREIGN PATENT DOCUMENTS

| | | |
|---|---|---|
| EP | 304063 | 2/1989 |
| JP | 08-092217 | 0/1996 |
| JP | 08-092217 | 4/1996 |
| WO | WO 99/32434 | 7/1999 |

OTHER PUBLICATIONS

Koichi Narasaka et al.: "Steroselective synthesis of meso(or erythro) 1, 3-diols from beta-hydroxyketones" Chemistry Letters, pp. 1415-1418, 1980.

Mikio Suzuki, et al., "Synthesis and Biological Evaluations of Quinoline-based HMG-CoA Reductase Inductors", Bioorganic & Medicinal Chemistry, vol. 9, No. 10, XP-002313788, 2001, pp. 2727-2743.

Koichi Narasaka et al.: "Stereoselective synthesis of meso (or erythro) 1, 3-diols from beta-hydroxyketones" Chemistry Letters, pp. 1415-1418. 1980

Kau-Ming Chen et al. "A Novel Method for the In Situ Generation of Alkoxydialkylobranes and Their Use in the Selective Preparation of 1, 3-Syn Diols" Chemistry Letters, pp. 1923-1926. 1987

* cited by examiner

METHOD FOR PREPARING A 7-QUINOLINYL-3,5-DIHYDROXYHEPT-6-ENOATE

TECHNICAL FIELD

The present invention relates to a method for preparing a 7-quinolinyl-3,5-dihydroxyhept-6-enoate.

More particularly, it relates to a method for industrially advantageously and efficiently preparing an (E)-7-[2-cyclopropyl-4-(4-fluorophenyl)-quinolin-3-yl]-3,5-dihydroxyhept-6-enoate which is useful as an intermediate for the synthesis of a HMG-CoA reductase inhibitor as a cholesterol-reducing agent

BACKGROUND ART

An (E)-7-[2-cyclopropyl-4-(4-fluorophenyl)-quinolin-3-yl]-3,5-dihydroxyhept-6-enoate is an intermediate which is useful as an intermediate for the synthesis of a HMG-CoA reductase inhibitor, and as its production method, the following method employing sodium borohydride (NaBH$_4$) is disclosed in JP-A-1-279866, U.S. Pat. No. 5,856,336 or EP0304063B1:

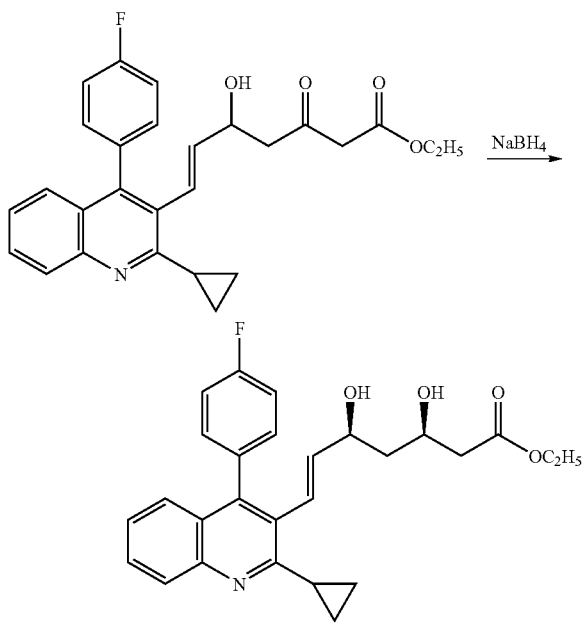

Further, it has heretofore been known that at the time of producing a 1,3-diol by reducing a β-hydroxyketone by sodium borohydride, a boron compound is permitted to be present, as in the present invention, whereby a selective reduction reaction will proceed, and 1) JP-A-61-40243 or EP0164049A2 discloses a reaction in the presence of a triethylborane, 2) Chemistry Letters, 1980, 1415, discloses a reaction in the presence of a tributylborane, and 3) Chemistry Letters, 1987, 1923, discloses a reaction in the presence of diethylmethoxyborane.

Further, at that time, for the treatment of the boron compound after completion of the reduction reaction, in 1) and 2), the reaction solution with the tetrahydrofuran reaction solvent is per se poured into a 30% aqueous solution of hydrogen peroxide, and then, a solvent which separates from water, is added to carry out an extraction operation to obtain a product, and in 3), after the completion of the reaction, methanol is added, and an azeotropic operation with methanol is carried out, followed by a usual extraction operation to obtain a product.

As in the foregoing, in the reduction reaction of a β-hydroxyketone in the presence of a boron compound, it is necessary to carry out treatment of the boron compound after completion of the reduction reaction in order to efficiently obtain the product.

By the method for treating the boron compound after completion of the reaction as reported in the above 1), 2) and 3), there is no particularly serious problem in the production in a small amount at a laboratory experimental level, but in scaling up, the methods of 1) and 2) have an environmental waste liquid treatment problem due to the use of a large amount of an aqueous solution of hydrogen peroxide, and by the method of 3), unless a large amount of methanol is used, treatment of the boron compound can not completely be carried out, and there is a difficulty from the viewpoint of the production efficiency. Thus, either method can hardly be regarded as an industrially advantageous production method.

Further, with respect to the compound of the present invention, it has also been found that in order to isolate the desired substance from the product obtained after completion of the reduction reaction, it is necessary to carry out the treatment of the boron compound after completion of the reduction reaction, and otherwise, the desires substance can not easily be isolated.

Accordingly, it is an object of the present invention to provide a method for simply and industrially advantageously preparing an (E)-7-[2-cyclopropyl-4-(4-fluorophenyl)-quinolin-3-yl]-3,5-dihydroxyhept-6-enoate.

DISCLOSURE OF THE INVENTION

The present inventors have conducted various studies to solve such problems and as a result, have found an industrially advantageous production method from the viewpoint of the above-mentioned waste liquid treatment and production efficiency and have arrived at the present invention.

That is, the present invention provides a method for preparing a 7-quinolinyl-3,5-dihydroxyhept-6-enoate represented by the formula (IV):

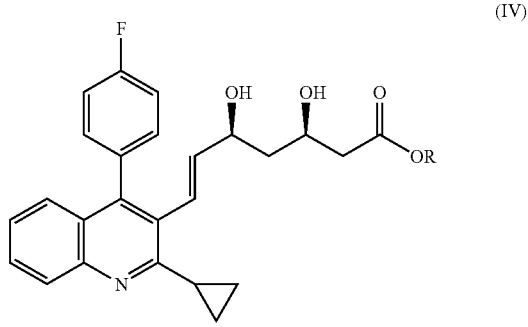

(wherein R represents an alkyl group or an aryl group), characterized in that a compound represented by the formula (I):

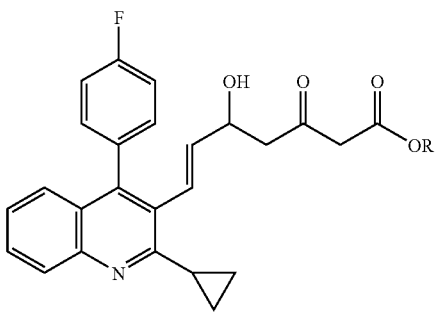

(wherein R is as defined above), or a compound represented by the formula (II):

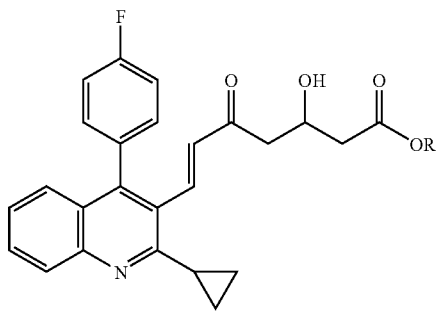

(wherein R is as defined above), is reduced by sodium borohydride in the presence of a boron compound represented by the formula (III):

R'OBR"$_2$                            (III)

(wherein R' and R" represent independently an alkyl group), and then the resultant reaction mixture is treated with an aqueous solution of hydrogen peroxide.

BEST MODE FOR CARRYING OUT THE INVENTION

Now, the present invention will be described in further detail.

Firstly, various terms used in this specification will be explained.

In this specification, "n" means normal, "i" iso, "s" secondary, "t" tertiary, "c" cyclo, "p" para, and "o" ortho.

Substituent R represents an alkyl group or an aryl group.

The alkyl group is a linear, branched or cyclic alkyl group and may, for example, be a $C_{1-4}$ alkyl group, such as methyl, ethyl, n-propyl, i-propyl, c-propyl, n-butyl, i-butyl, s-butyl, t-butyl, c-butyl, 1-methyl-c-propyl or 2-methyl-c-propyl.

The aryl group may, for example, be a phenyl group.

As substituent R, preferably, methyl and ethyl are, for example, mentioned.

Substituents R' and R" represent independently an alkyl group.

Such an alkyl group is a linear, branched or cyclic alkyl group and may, for example, be a $C_{1-4}$ alkyl group such as methyl, ethyl, n-propyl, i-propyl, c-propyl, n-butyl, i-butyl, s-butyl, t-butyl, c-butyl, 1-methyl-c-propyl or 2-methyl-c-propyl.

As substituents R' and R", preferably, methyl and ethyl are, for example, mentioned.

The compound represented by the formula (I) or (II) as the starting material, can be produced by e.g. the methods disclosed in JP-A-1-279866, JP-A-8-92217 and JP-A-8-127585.

The present invention is applicable to a production method wherein the compound represented by the formula (I) or (II) as the starting material, is an optically active substance. As such an optically active substance, 5S-form (I) or 3R-form (II) may be mentioned.

As the boron compound of the formula (III), a commercial product may usually be used. For example, diethylmethoxyborane, dibutylmethoxyborane, diethylethoxyborane or dibutylethoxyborane may be mentioned. Preferably, diethylmethoxyborane may be mentioned.

The amount of the boron compound to be used is within a range of from 0.1 mol time to 5 mol times, preferably within a range of from 0.8 mol time to 3 mol times, more preferably within a range of from 1 mol time to 1.5 mol times, based on the substrate of the starting material.

The amount of sodium borohydride as the reducing agent to be used, is within a range of from 0.5 mol time to 5 mol times, preferably within a range of from 0.8 mol time to 2.5 mol times, based on the substrate of the starting material.

The solvent to be used for the reduction reaction is not particular limited so long as it is inert to the reaction. For example, an aromatic hydrocarbon such as benzene, toluene, xylene, mesitylene, chlorobenzene or o-dichlorobenzene, an aliphatic hydrocarbon such as n-hexane, cyclohexane, n-octane or n-decane, a halogenated hydrocarbon such as dichloromethane, dichloroethane, chloroform or carbon tetrachloride, an ether such as tetrahydrofuran (THF), diethyl ether, t-butyl methyl ether or dimethoxyethane, or an alcohol such as methanol, ethanol, n-propanol, i-propanol or n-butanol, may, for example, be mentioned. Preferably, toluene, tetrahydrofuran (THF) or methanol may, for example, be mentioned. More preferred is a mixed solvent of tetrahydrofuran and methanol.

The amount of the solvent for the reaction to be used, is within a range of from 2 mass times to 100 mass times, preferably within a range of from 5 mass times to 30 mass times, based on the substrate of the starting material.

The reaction temperature is usually within a range of from −100° C. to 0° C., preferably within a range of from −100° C. to −30° C., more preferably within a range of from −90° C. to −60° C.

The reaction mode of the reduction by sodium borohydride in the present invention may be either one wherein the substrate of the formula (I) or (II) and the boron compound of the formula (III) are dissolved in a solvent, and then, at a set temperature, sodium borohydride may be added, or a method wherein the boron compound of the formula (III) and sodium borohydride are firstly put into a solvent, and then, the substrate of the formula (I) or (II) is dropwise added thereto.

The present invention is characterized in that after completion of the reduction reaction, treatment with an aqueous solution of hydrogen peroxide is carried out for the treatment of the boron compound. However, in a case where an aromatic hydrocarbon, an aliphatic hydrocarbon, a halogenated hydrocarbon, a water-insoluble ether or the like is used as the solvent for the reaction, it is preferred that the reaction mixture is once subjected to water washing treatment and then, an aqueous solution of hydrogen peroxide is added thereto to carry out the treatment.

Further, in a case where a water-soluble solvent such as tetrahydrofuran or an alcohol is used for the reduction reaction, it is preferred that a solvent which separates from water, such as toluene is once added, and the solvent for reaction which is soluble in water is distilled off, whereupon an aqueous solution of hydrogen peroxide is added to carry out the treatment.

As the solvent for the treatment with an aqueous solution of hydrogen peroxide, a solvent which separates from water, is preferred. For example, an aromatic hydrocarbon such as benzene, toluene, xylene, mesitylene, chlorobenzene or o-dichlorobenzene, an aliphatic hydrocarbon such as n-hexane, cyclohexane, n-octane or n-decane, or a halogenated hydrocarbon such as dichloromethane, dichloroethane, chloroform or carbon tetrachloride, may, for example, be mentioned. Preferably, toluene may be mentioned.

The amount of the solvent to be used is within a range of from 2 mass times to 100 mass times, preferably within a range of from 5 mass times to 30 mass times, based on the substrate of the starting material.

With respect to the aqueous solution of hydrogen peroxide, the concentration is not particularly limited, but from the viewpoint of the handling efficiency, etc., a commercially available 35% hydrogen peroxide aqueous solution which is easy to handle, is usually preferred.

The amount of the aqueous solution of hydrogen peroxide to be used may be large excess in order to accelerate the reaction, but from the viewpoint of the environment, it is within a range of from an equal mol time to 50 mol times, preferably within a range of from an equimol time to 20 mol times, based on the substrate.

The temperature is within a range of from 0° C. to 100° C., preferably within a range of from 10° C. to 50° C.

The treating time may vary depending upon the solvent to be used, the amount of hydrogen peroxide and the temperature, but is from 1 to 100 hours.

Further, it is possible to accelerate the reaction by permitting an inorganic base to be present at the time of the treatment with an aqueous solution of hydrogen peroxide.

The inorganic base may, for example, be a hydroxide such as sodium hydroxide, potassium hydroxide, magnesium hydroxide or calcium hydroxide, or a carbonate such as sodium carbonate, potassium carbonate, magnesium carbonate or calcium carbonate. Preferably, sodium carbonate or potassium carbonate may be mentioned.

The amount of the inorganic base to be used is within a range of from 0.1 mol time to 20 mol times, preferably within a range of from 0.5 mol time to 5 mol times, based on the substrate.

After completion of the reaction, an aqueous solution of hydrogen peroxide is separated, and then, water washing treatment is further carried out, and if necessary, treatment with a reducing agent such as sodium sulfite, is carried out, followed by recrystallization from toluene or a mixed solvent of toluene with another solvent, to isolate an (E)-7-[2-cyclopropyl-4-(4-fluorophenyl)-quinolin-3-yl]-3,5-dihydroxyhept-6

Further, if necessary, recrystallization from a mixed solvent of ethyl acetate and n-heptane is carried out to obtain a highly pure (E)-7-[2-cyclopropyl-4-(4-fluorophenyl)-quinolin-3-yl]-3,5-dihydroxyhept-

EXAMPLES

Now, the present invention will be described in detail with reference to Examples, but the present invention is by no means restricted by such Examples.

Here, the quantitative analysis of an (E)-7-[2-cyclopropyl-4-(4-fluorophenyl)-quinolin-3-yl]-3,5-dih by means of HPLC (high performance liquid chromatography) was carried out under the following conditions.

Column: L-Column ODS (manufactured by Foundation Chemical Evaluation and Research Institute, Japan)
Eluent: Ethanol/THF/0.01 M ammonium acetate=45/3/52
Column temperature: 40° C.
Flow rate: 1.0 mL/min
Measuring wavelength: 254 nm
Retention time: About 27 minutes Example 1

After flushing a reactor flask with nitrogen, ethyl (E)-7-[2-cyclopropyl-4-(4-fluorophenyl)-quinolin-3-yl]-5-hydroxy-3-oxohept-6-enoate (herein MOLE) (29.90 g, 66.8 mmol) was dissolved in THF (148.7 g) and methanol (54.9 g), followed by cooling to −75° C.

After flushing another reactor flask with nitrogen, THF (43.2 g) and diethylmethoxyborane (1.0 M/THF solution, 80 mL) were charged, and sodium borohydride (3.31 g, 87.5 mmol) was further added. The resultant suspension was cooled to −75° C., and the previous MOLE/THF/methanol solution was dropwise added thereto at a temperature of from −75° C. to −70° C.

After completion of the dropwise addition, stirring was further continued for 1 hour at −75° C., and then the reaction solution was dropwise added to a reactor flask having acetic acid (6.5 mL) and toluene (10 g) charged to quench the reaction.

The reaction solution was heated to a temperature of from 35° C. to 40° C., and then, THF and methanol were distilled off under reduced pressure. After the distilling off, toluene (311 g) was added for dissolution, and the organic layer was washed twice with water (230 g).

As a result, 379.6 g of an organic layer was obtained.

The obtained organic layer was quantified by HPLC, whereby a reduced form of the product (inclusive of a borane-coordinated form) was contained in an amount of 27.93 g (yield: 93%).

Further, the organic layer was examined by NMR for the product ethyl (E)-7-[2-cyclopropyl-4-(4-fluorophenyl)-quinolin-3-yl]-3,5-dihydroxyhept-6-enoate (hereinafter referred to simply as DOLE) and its borane-coordinated form, whereby 20% of the borane-coordinated form was found to be present.

Then, out of the obtained organic layer, 17.7 g (containing 1.30 g, 2.9 mmol, of DOLE) was taken, and anhydrous sodium carbonate (307 mg, 2.9 mmol) and a 35% hydrogen peroxide aqueous solution (2.8 g, 29 mmol) were added thereto, followed by stirring at a temperature of from 30° C. to 35° C. for 3 hours.

The reaction solution was examined by NMR for the borane-coordinated form, whereby it was found to be 0%.

After completion of the treatment with the hydrogen peroxide aqueous solution, liquid separation was carried out, and water (3.8 g) was further added for washing with water, followed by washing with a 4% sodium pyrosulfite aqueous solution (4.0 g) and then further by washing twice with water (3.8 g).

The obtained organic layer was quantified by HPLC, whereby DOLE was contained in an amount of 1.28 g.

The organic layer was heated to a temperature of from 40° C. to 50° C., and then, toluene was distilled off under reduced pressure.

After the distilling off, the product was recrystallized from ethyl acetate (2.56 g) and n-heptane (4.39 g) to obtain 1.22 g of DOLE as crystals.

Example 2

Out of 379.6 g of the organic layer containing 27.93 g of the product (inclusive of 20% of the borane-coordinated form), obtained in Example 1, 17.7 g (containing 1.30 g, 2.9 mmol, of DOLE) was taken, and a 50% potassium carbonate aqueous solution (800 mg, 2.9 mmol) and a 35% hydrogen peroxide aqueous solution (2.8 g, 29 mmol) were added thereto, followed by stirring for 3 hours at a temperature of from 30° C. to 35° C.

The reaction solution was examined by NMR for the borane-coordinated form, whereby it was 0%.

After completion of the treatment with the hydrogen peroxide aqueous solution, washing with water, etc. were carried out in the same manner as in Example 1.

The obtained organic layer was quantified by HPLC, whereby DOLE was contained in an amount of 1.20 g.

The organic layer was heated to a temperature of from 40° C. to 50° C., and then, toluene was distilled off under reduced pressure.

After the distilling off, the product was recrystallized from ethyl acetate (2.56 g) and n-heptane (4.39 g) to obtain 1.14 g of DOLE as crystals.

Reference Example 1

Out of 379.6 g of the organic layer containing 27.93 g of the product (inclusive of 20% of the borane-coordinated form), obtained in Example 1, 17.7 g (containing 1.30 g, 2.9 mmol, of DOLE) was taken and directly heated to a temperature of from 40° C. to 50° C. without subjecting it to treatment with a hydrogen peroxide aqueous solution of the present invention, and then, toluene was distilled off under reduced pressure.

After the distilling off, the product was tried to be recrystallized from ethyl acetate (2.56 g) and n-heptane (4.39 g), but was not crystallized, and an oil layer was simply separated, whereby it was impossible to isolate DOLE as crystals.

INDUSTRIAL APPLICABILITY

According to the present invention, it is possible to produce an (E)-7-[2-cyclopropyl-4-(4-fluorophenyl)-quinolin-3-yl]-3,5-dihydroxyhept-6-enoate w intermediate useful for the synthesis of a HMG-COA reductase inhibitor, in good yield and industrially advantageously.

The invention claimed is:

1. A method for preparing a 7-quinolinyl-3,5-dihydroxyhept-6-enoate represented by the formula (IV):

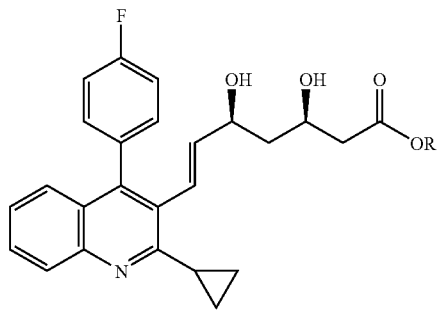

(wherein R represents an alkyl group or an aryl group), characterized in that a compound represented by the formula (I):

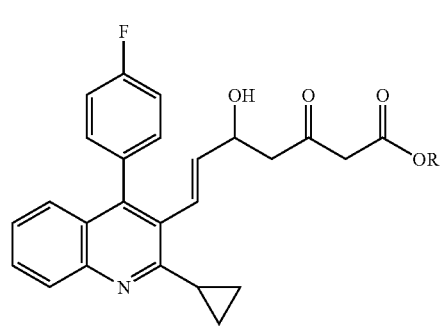

(wherein R is as defined above), or a compound represented by the formula (II):

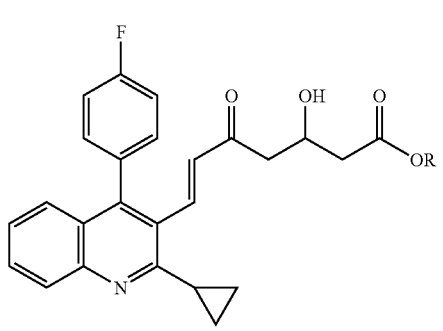

(wherein R is as defined above), is reduced by sodium borohydride in a reaction solvent in the presence of a boron compound represented by the formula (III):

R'OBR''$_2$     (III)

(wherein R' and R'' represent independently an alkyl group), the reaction solvent is removed, and then the resultant reaction mixture is treated with an aqueous solution of hydrogen peroxide in the presence of an inorganic base in a two phase system with an organic solvent with separates from water.

2. The method according to claim 1, wherein the compound represented by the formula (I) or (II) is an optically active substance.

3. The method according to claim 1, wherein in the formula (III), R' is a methyl group, and R" is an ethyl group.

4. The method according to claim 1, wherein the inorganic base is sodium carbonate or potassium carbonate.

5. The method according to claim 1, wherein the organic solvent which separates from water, is toluene.

6. The method according to claim 1, wherein the 7-quinolinyl-3,5-dihydroxyhept-6-enoate represented by the formula (IV) is isolated by recrystallization after said treatment with the aqueous solution of hydrogen peroxide.

* * * * *